United States Patent
Lu et al.

(10) Patent No.: US 7,020,523 B1
(45) Date of Patent: Mar. 28, 2006

(54) METHODS AND SYSTEMS FOR AUTOMATICALLY SWITCHING ELECTRODE CONFIGURATIONS

(75) Inventors: Richard Lu, Thousand Oaks, CA (US); Corey Brown, Los Angeles, CA (US)

(73) Assignee: Pacesetter, Inc., Sylmar, CA (US)

(*) Notice: Subject to any disclaimer, the term of this patent is extended or adjusted under 35 U.S.C. 154(b) by 627 days.

(21) Appl. No.: 10/125,079

(22) Filed: Apr. 16, 2002

(51) Int. Cl.
*A61N 1/368* (2006.01)

(52) U.S. Cl. ..................................... 607/27
(58) Field of Classification Search ............... 600/373, 600/374, 377, 393, 508, 509; 607/4, 5, 9, 607/27, 28, 116, 119, 722, 123
See application file for complete search history.

(56) References Cited

U.S. PATENT DOCUMENTS

| | | | | |
|---|---|---|---|---|
| 5,766,229 A | * | 6/1998 | Bornzin | 607/28 |
| 6,782,291 B1 | * | 8/2004 | Bornzin et al. | 607/28 |
| 6,876,882 B1 | * | 4/2005 | Obel et al. | 607/25 |
| 2003/0083708 A1 | * | 5/2003 | Bradley et al. | 607/27 |
| 2004/0030359 A1 | * | 2/2004 | Spinelli et al. | 607/27 |

* cited by examiner

*Primary Examiner*—Robert E. Pezzuto
*Assistant Examiner*—Frances P. Oropeza

(57) ABSTRACT

Various embodiments can permit electrode configurations that are used in implantable devices to be automatically changed. In some embodiments, configurations that are used to ascertain capture (ventricular and/or atrial) can be automatically changed by a stimulation device and then automatically configured for use. Various parameters associated with the electrical configurations can be automatically calibrated so that a stimulation device's automatic capture feature can continue to function notwithstanding the fact that an electrode configuration change has taken place.

22 Claims, 9 Drawing Sheets

METHODS AND SYSTEMS FOR AUTOMATICALLY SWITCHING ELECTRODE CONFIGURATIONS

TECHNICAL FIELD

This invention relates to methods and systems for automatically switching electrode configurations in an implantable stimulation device and, in particular embodiments, ascertaining whether ventricular and/or atrial capture has occurred in a heart patient.

BACKGROUND

Implantable cardiac stimulation devices, such as pacemakers and implantable cardioverter-defibrillators, are devices that are implanted within the body of a patient so as to correct and regulate heart function. Typically, these types of devices include one or more leads that are adapted to be implanted within the body of the patient so as to be adjacent the heart in order to deliver therapeutic electrical stimulation pulse to the heart. These devices typically include a control unit having a processor, that is positioned within a casing that is also adapted to be implanted within the body of the patient. Over time, the control units of implantable cardiac devices have become increasingly sophisticated thereby allowing the control units to tailor the therapeutic electrical stimulation that is provided to the heart to optimize device performance and heart regulation.

For example, current generation pacemakers are capable of detecting intrinsic heart activity so that the pacemaker only provides pacing pulses when the intrinsic heart activity is missing. These types of more sophisticated implantable cardiac devices also incorporate numerous sensors which provide data to the control unit enabling the control unit to optimize the therapeutic stimulation provided to the heart.

Implantable cardiac devices also generally include telemetry circuits that allow a treating physician to download instructions to the control unit following implantation. The telemetry circuit can also be used to allow the treating physician to retrieve stored information about heart activity and device performance. The treating physician may periodically want to review device performance or heart activity data to ensure that the device is providing therapy in desired manner. Consequently, current generation implantable cardiac devices incorporate memories, and the processors in these devices are adapted to periodically sample and record various performance parameter measurements in the storage means.

In heart stimulation, an electrical pulse, i.e. a heart stimulation pulse, is delivered to heart tissue in the atrium and/or ventricle for the purpose of inducing contraction of the atrium and/or the ventricle, thereby supporting the heart's pumping capacity. "Capture" refers to the depolarization of heart cells produced by a stimulation pulse. Depolarization (usually) results in the contraction of heart tissue. The lowest energy content needed to achieve depolarization of heart cells is usually referred to as the "stimulation threshold" or "capture threshold". The response of heart tissue to a stimulation pulse is referred to as "evoked response", (ER) which can be capture or non-capture.

Typically, then, many stimulation devices sample for an evoked response signal to determine whether capture has indeed occurred. Specifically, the stimulation device can be configured to periodically provide a series of pacing pulses of decreasing magnitude to determine at what magnitude the delivered pacing pulse fails to induce a captured evoked (or captured beat) response. The last magnitude value that resulted in a captured evoked response is known as the capture threshold. The value corresponding to the capture threshold can then be used to set the magnitude of the pacing pulse to be delivered to the heart at some safety margin above the capture threshold. This can ensure that the delivered pacing pulse induces a captured evoked response. This type of functionality is referred to as "automatic capture".

In automatic capture pacing devices, the output is typically set to a value which is much closer to the threshold value, since more frequent capture threshold measurements are continuously being made to ensure that the output will be adequate to obtain capture even as changes in the capture threshold varies, which may be indicative of a developing problem with the lead or alterations in the clinical status of the patient. The capture thresholds are often recorded in the memory for subsequent review and analysis by the treating physician to detect these changes in threshold value which, as noted above, may be indicative of lead and implantation conditions.

In some devices, the capture threshold is measured on a relatively frequent basis for automatic capture type devices, e.g., once or twice a day, and the resulting measurement may be recorded in memory on a somewhat less frequent periodic basis, e.g., once or twice a week. The stimulation output is adjusted accordingly following a capture threshold measurement.

This invention arose out of concerns associated with providing improved stimulation methods and stimulation devices. In particular, this invention arose out of concerns associated with providing improved automatic capture stimulation devices and methods.

SUMMARY

Various embodiments can permit electrode configurations that are used in implantable devices to be automatically changed. In some embodiments, configurations that are used to ascertain capture (ventricular and/or atrial) can be automatically changed by a stimulation device and then automatically configured for use. Various parameters associated with the electrical configurations can be automatically calibrated so that a stimulation device's automatic capture feature can continue to function notwithstanding the fact that an electrode configuration change has taken place.

BRIEF DESCRIPTION OF THE DRAWINGS

Further features and advantages of the claimed embodiments can be more readily understood by reference to the following description taken in conjunction with the accompanying drawings, in which:

DETAILED DESCRIPTION

The following description is of the best mode presently contemplated for practicing the described embodiments. This description is not to be taken in a limiting sense, but rather is made merely for the purpose of describing the general principles of the inventive embodiments. The scope of the described embodiments should be ascertained with reference to the issued claims. In the description of the embodiments that follow, like numerals or reference designators will be used to refer to like parts or elements throughout.

Overview

Some of the embodiments described below permit electrode configurations that are used to ascertain capture (ventricular and/or atrial) to be automatically changed. Parameters associated with the electrical configurations can be automatically calibrated so that a stimulation device's automatic capture feature can continue to function notwithstanding the fact that an electrode configuration change has taken place. This promotes convenience and flexibility on the part of heart patients in whom the stimulation devices are implanted. Otherwise, the device must disable the automatic capture function upon a change of the electrode configuration. An office visit is then required for the automatic capture function to be enabled again by a clinician using a programmer. Automatically changing electrode configurations can be useful in other contexts, as will become apparent below.

Exemplary Stimulation Device

The techniques that are described below are intended to be implemented in connection with a stimulation device that is configured or configurable to stimulate or shock a patient's heart.

Figure 1:
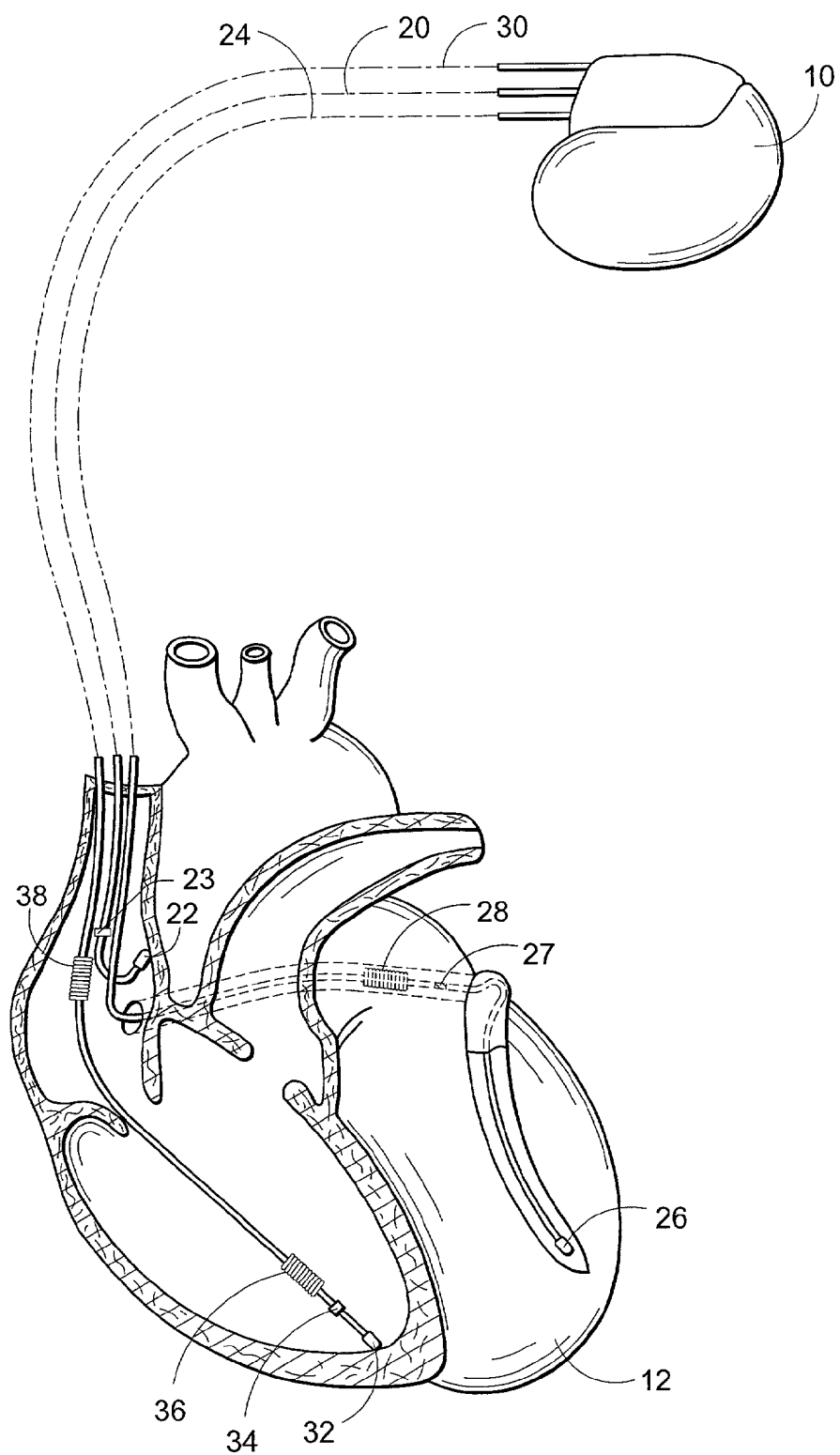
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, stimulation device 10 is coupled to an implantable right atrial lead 20 having at least an atrial tip electrode 22, which typically is implanted in the patient's right atrial appendage. The right atrial lead can also have a ring electrode 23 positioned above the atrial tip electrode 22.

To sense left atrial and ventricular cardiac signals and to provide left chamber pacing therapy, stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

Stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
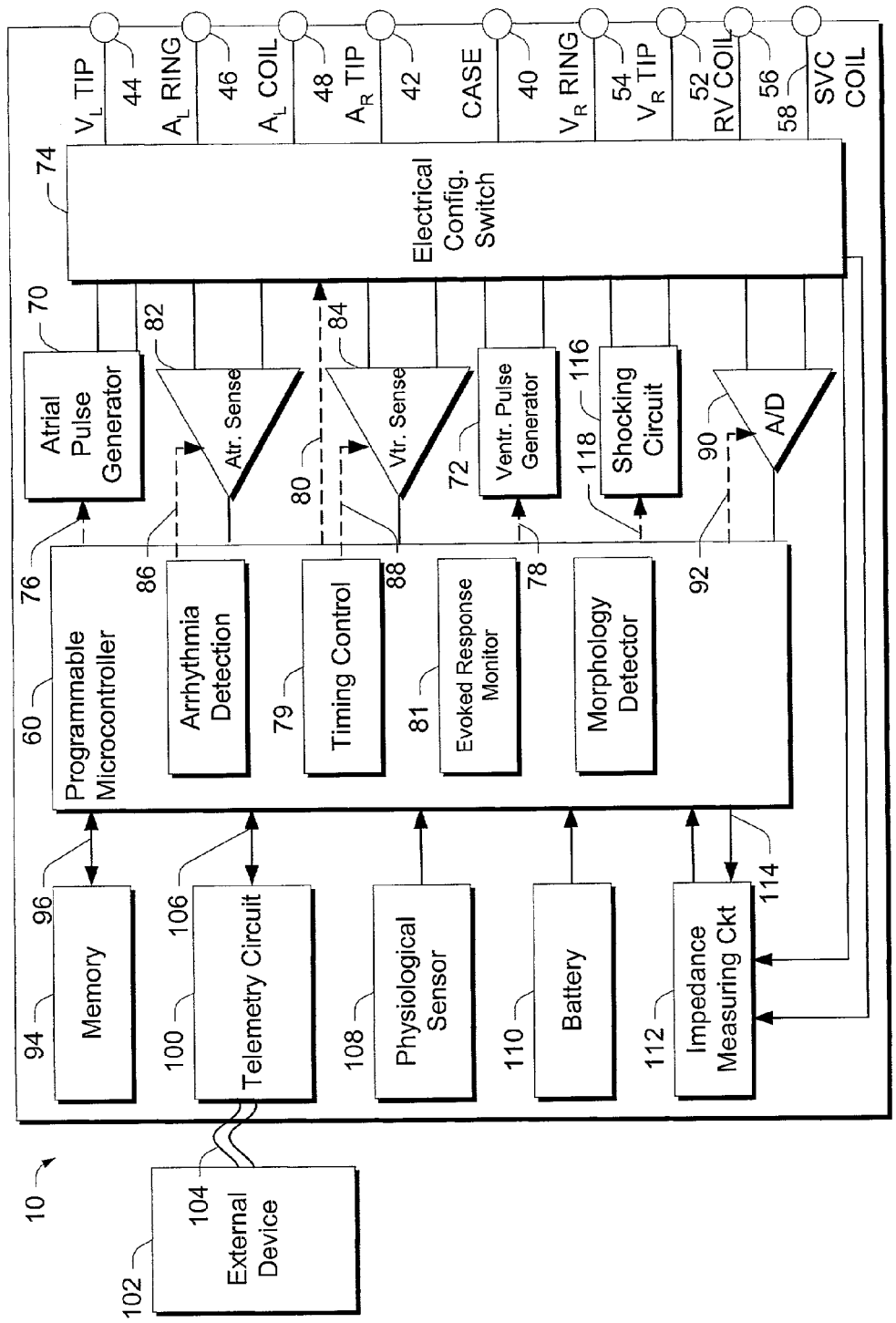
FIG. 2 is a functional block diagram of a multi-chamber implantable stimulation device illustrating the basic elements of a stimulation device which can provide cardioversion, defibrillation and pacing stimulation in four chambers of the heart.

FIG. 2 shows an exemplary, simplified block diagram depicting various components of stimulation device 10. The stimulation device can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the inventive techniques and methods described below can be implemented in connection with any suitably configured or configurable stimulation device. Accordingly, one of skill in the art could readily duplicate, eliminate or disable the appropriate circuitry in any desired combination to provide a device capable of treating the appropriate chamber(s) with cardioversion, defibrillation and pacing stimulation.

Housing 40 for stimulation device 10 is often referred to as the "can", "case" or "case electrode", and may be programmably selected to act as the return electrode for all "unipolar" modes. There may be multiple electrode positioned on or otherwise supported by the housing. The multiple electrodes can be used for impedance measurements. Housing 40 may further be used as a return electrode alone or in combination with one or more of the coil electrodes, 28, 36 and 38, for shocking purposes. Housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design and operation of the microcontroller 60 are not critical to the described embodiments. Rather, any suitable microcontroller 60 may be used that carries out the functions described herein. The use of microprocessor-based control circuits for performing timing and data analysis functions are well known in the art.

FIG. 2 also shows an atrial pulse generator 70 and a ventricular pulse generator 72 which generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

Microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 60 further includes an evoked response monitor 81 that can be utilized by the stimulation device 10 for monitoring various electrode configurations that are used to measure the evoked response. Response to a particular electrode configuration becoming inoperable, the evoked response monitor can cause a new electrode configuration to be automatically selected and configured to replace the previous electrode configuration.

A switch 74 includes a plurality of switches for connecting the desired electrodes to the appropriate I/O circuits, thereby providing complete electrode programmability. Accordingly, switch 74, in response to a control signal 80 from the microcontroller 60, determines the polarity of the stimulation pulses (e.g., unipolar, bipolar, combipolar, etc.) by selectively closing the appropriate combination of switches (not shown). Switch 74 is also used by the evoked response monitor to change an electrode configuration that is utilized for measuring the evoked response.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. One feature of the described embodiments is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 can further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer (e.g. a three-dimensional accelerometer) or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the described embodiments and is shown only for completeness.

The described embodiments can utilize a "sleep state" or diurnal sensor that can detect sleep, rest, and wake states. One such sensor is known as "activity variance" wherein an activity sensor is monitored diurnally to detect the low variance in the measurement corresponding to the sleep state.

The stimulation device additionally includes a battery 110 that provides operating power to all of the circuits shown in FIG. 2. For the stimulation device 10, which employs shocking therapy, the battery 110 is capable of operating at low current drains for long periods of time (e.g. preferably less than 10 µA), and is capable of providing high-current pulses (for capacitor charging) when the patient requires a shock pulse (e.g. preferably, in excess of 2 A, at voltages above 2 V, for periods of 10 seconds or more). The battery 110 also desirably has a predictable discharge characteristic so that elective replacement time can be detected. Accordingly, the device 10 preferably employs lithium/silver vanadium oxide batteries, as is true for most (if not all) current devices.

The stimulation device 10 can further include magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

FIG. 2 also shows an impedance measuring circuit 112 which is enabled by the microcontroller 60 via a control signal 114. Uses for an impedance measuring circuit 112 can include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. In the embodiments described below, the impedance measuring circuit 112 is additionally used to ascertain when a particular electrode configuration that used for ascertaining an evoked response is no longer able to reliably function in this capacity.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Measuring Evoked Response

As noted above, an evoked response is the depolarization of the myocardium as a result of a pulse generator output pulse. The evoked response can also be referred to as the "evoked response signal". Typically, the evoked response signal is measured via a pair of electrodes comprising part of the stimulation device. As an example, consider FIG. 3.

Figure 3:
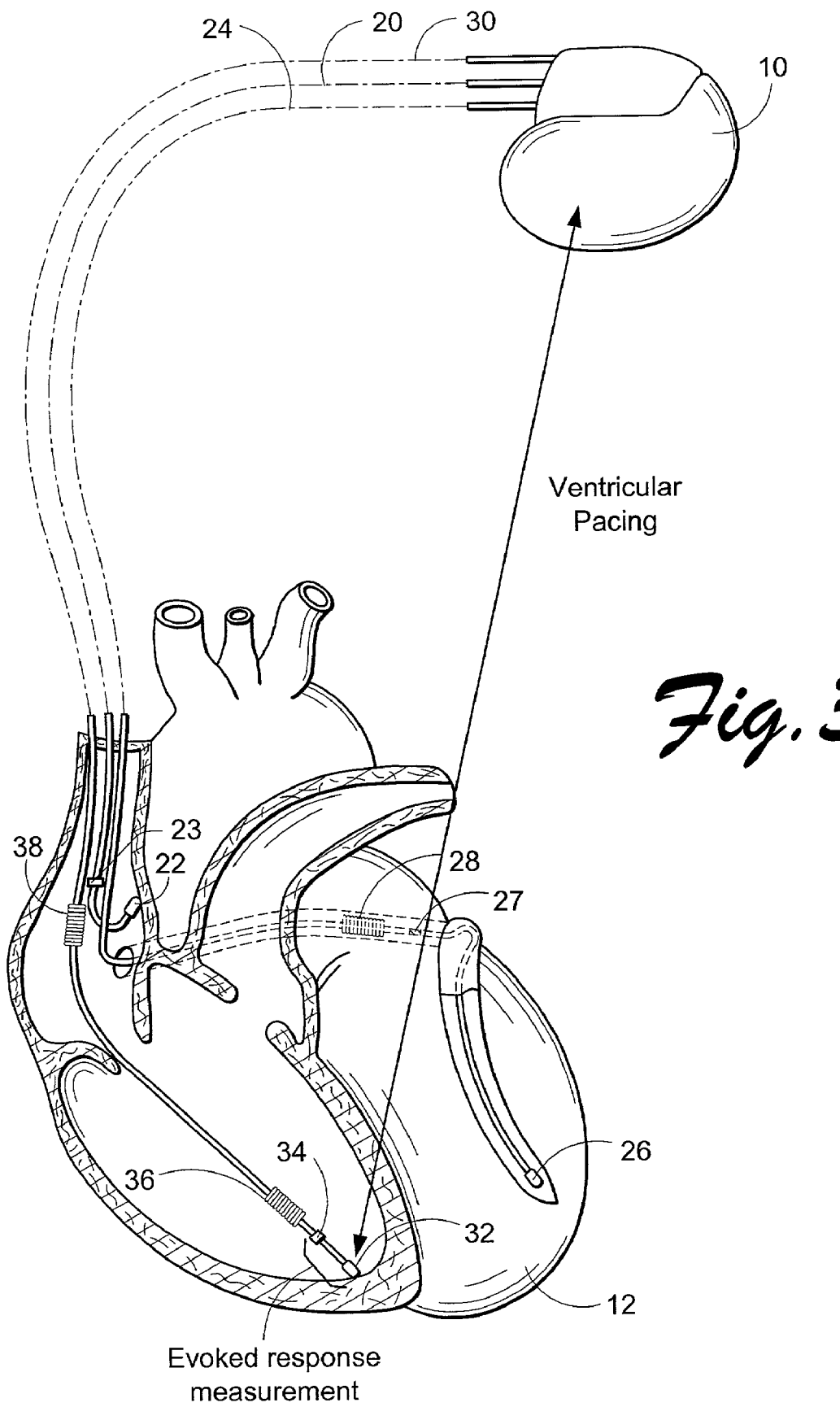
FIG. 3 is a diagram of the FIG. 1 stimulation device and illustrates an exemplary electrode configuration for ascertaining whether ventricular capture has occurred.

FIG. 3 shows the FIG. 1 stimulation device configured in an arrangement where ventricular pacing takes place via a unipolar configuration between tip electrode 32 and the can or case. Evoked response measurements take place in this particular configuration between the tip electrode 32 and the ring electrode 34. In this particular arrangement, a bipolar lead is used for the purpose of measuring the evoked response signal.

Before the automatic capture feature is enabled or turned on for this configuration (or any other configuration), an evoked response test and a calibration procedure is typically performed to calibrate parameters associated with the configuration. This helps to ensure that the evoked response signals that are ultimately measured using that configuration and which are used for the automatic capture feature are accurately processed. In this particular configuration, the evoked response signal is processed by examining the slope or slew rate of the evoked response signal. Essentially, in this configuration, and because the electrodes between which the evoked response signal is measured are located fairly close together, the slope or slew rate of the evoked response signal will be fairly steep. This makes it ideal to use for ascertaining whether capture has occurred. The techniques by which the evoked response are measured using a bipolar configuration are known and understood by those of skill in the art. Accordingly, for the purposes of brevity, they are not discussed further herein.

There are electrode configurations, however, where due to the characteristic of the evoked response signal that is received by the electrodes, the slope or slew rate is not the first choice for use in ascertaining whether capture has occurred. Consider, for example, FIG. 4.

Figure 4:
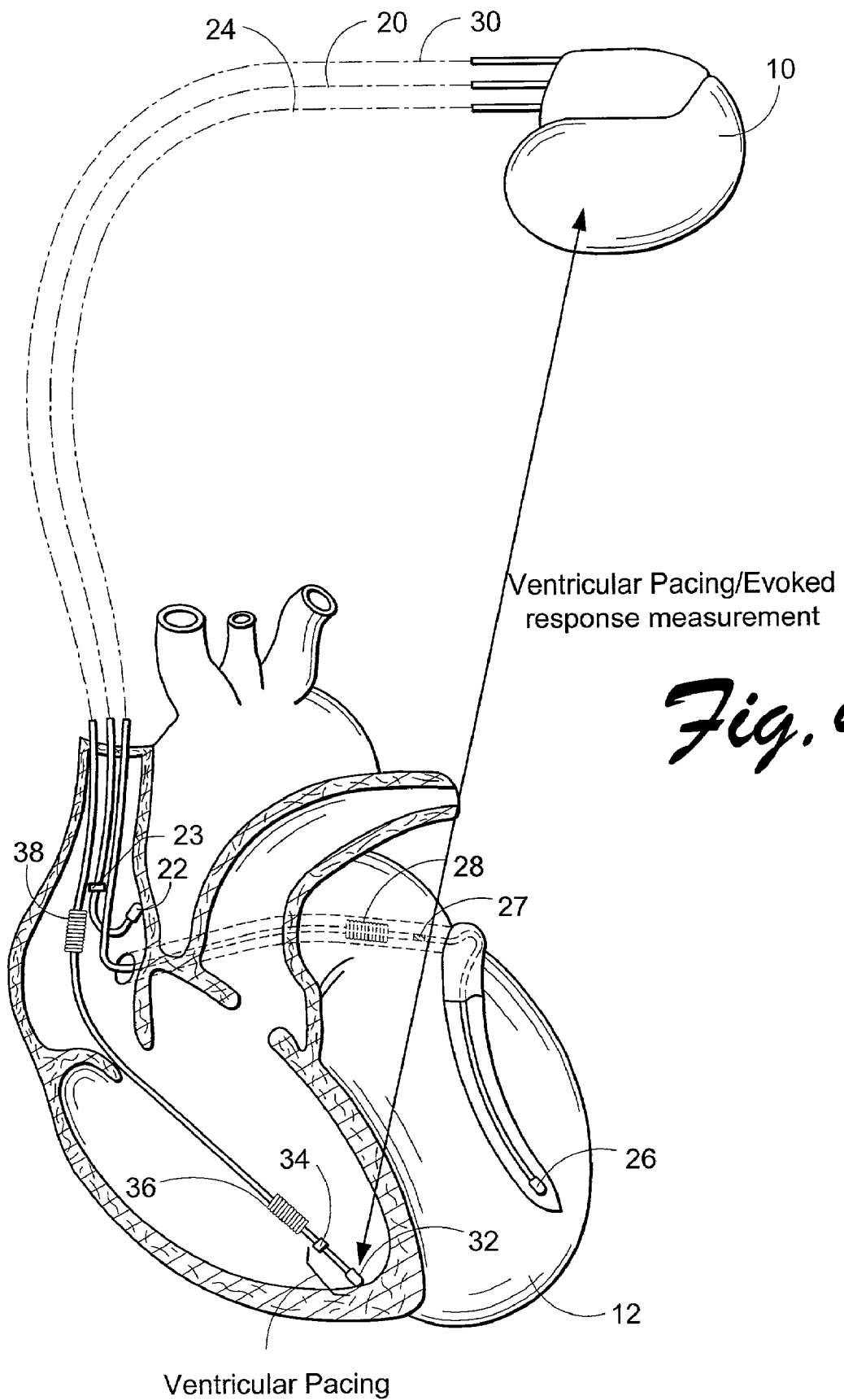
FIG. 4 is a diagram of the FIG. 1 stimulation device and illustrates another exemplary electrode configuration for ascertaining whether ventricular capture has occurred.

FIG. 4 shows the FIG. 1 stimulation device configured in a manner such that ventricular pacing can take place either using a bipolar configuration (i.e. between tip electrode 32 and ring electrode 34) or a unipolar configuration (i.e. between tip electrode 32 and the can or case). Evoked response measurements take place, in this arrangement, through the unipolar configuration (i.e. between tip electrode 32 and the can or case). Notice, however, in this case that the evoked response measurements take place between a different pair of electrodes. Whereas in the case of FIG. 3 the evoked response measurements take place between the tip and ring electrodes 32, 34 respectively, the evoked response measurements now take place between tip electrode 32 and the can or case.

Understandably, in this different evoked response configuration, the same measurement parameters cannot be used without modification. For example, due to the fact that the electrodes relative to which the evoked response signal is measured are located a greater distance than in the FIG. 3 configuration, the characteristics of the evoked response signal are different (i.e. the evoked response signal that the sensing electrodes will see). More specifically, the evoked response signal is now somewhat more stretched out than in the FIG. 3 example. This different characteristic makes it less desirable to use the slope or the slew rate of the evoked response signal to ascertain whether capture has occurred. Rather, as will be appreciated and understood by those of skill in the art, it is more desirable in this configuration to use a measure called the "paced depolarization integral" or "PDI". The PDI is defined as an integration of the evoked R-wave. Accordingly, when this different method is used to ascertain whether capture has occurred, parameters that are associated with this method are initially tested and calibrated, as in the previous case.

The reader should appreciate the following at this point. First, there are multiple different electrode configurations that can be used for measuring the evoked response signal for purposes of ascertaining whether capture has occurred. Each of these different configurations can typically use a different method for measuring and analyzing the evoked response signal. In one example, this method can involve looking at the slope or slew rate of the evoked response signal. In another example, this method can involve looking at the pace depolarization integral of the evoked response signal. When a particular method is used, the stimulation device typically tests the electrode configuration and calibrates parameters associated with the method before it is used in connection with an automatic capture feature, so that the method can accurately process the evoked response signal.

Automatically Switchable Electrode Configuration for Determining Evoked Response In accordance with the described embodiments, systems and methods are provided that automatically switch to a different electrode configuration for measuring the evoked response signal. In the described embodiments, measurement of the evoked response signal takes place in conjunction with providing an automatic capture feature. Accordingly, stimulation devices can be provided that automatically switch electrode configurations and adapt those configurations so that the automatic capture feature can continue to be used. The electrode configurations can typically be switched because of perceived operability problems associated with a current electrode configuration.

Figure 5:
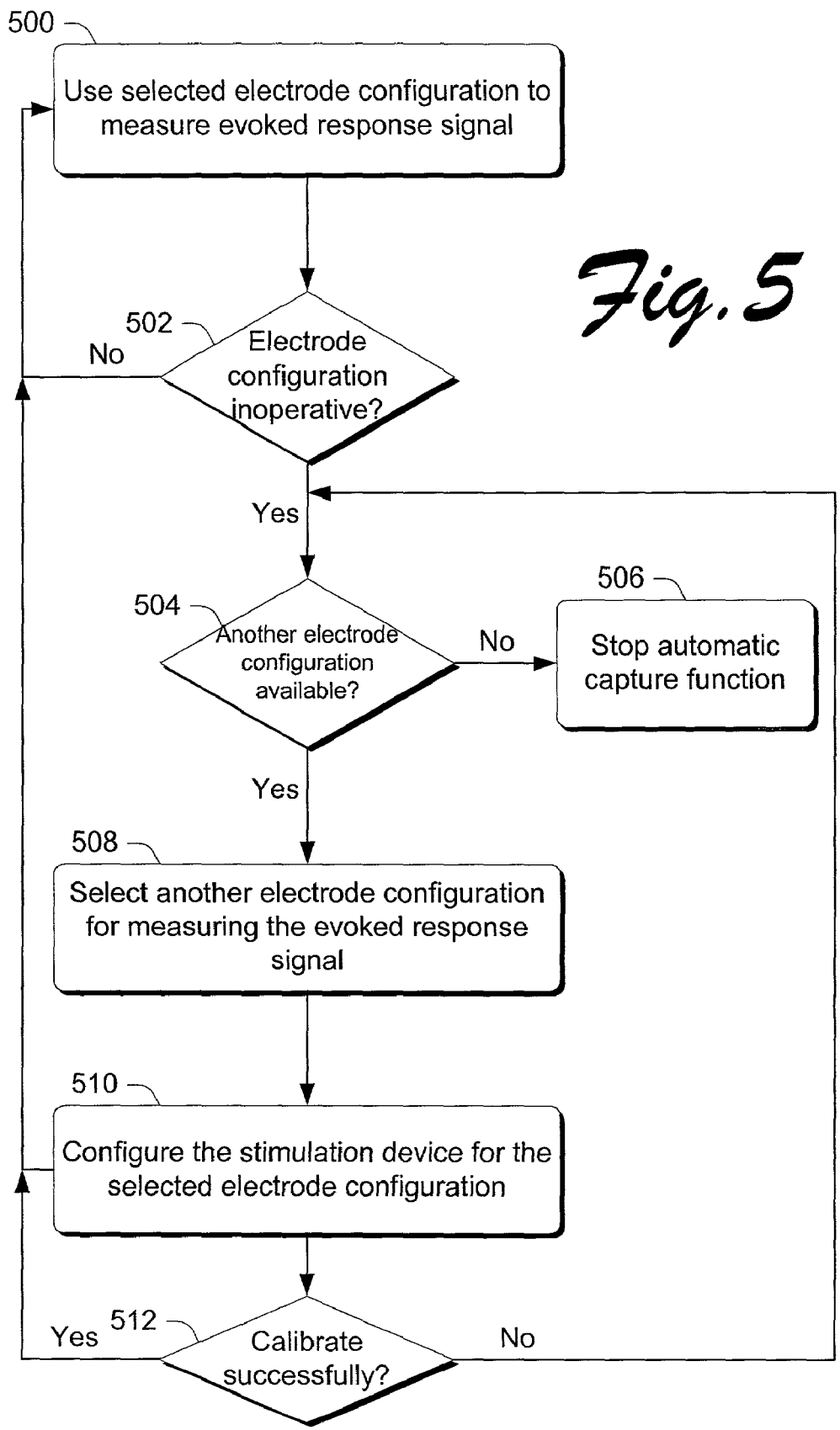
FIG. 5 is a flow diagram that describes steps in a method in accordance with one embodiment.

FIG. 5 is a flow diagram that describes steps in a method in accordance with one embodiment. The steps can be implemented in any suitable hardware, software, firmware, or combination thereof. In the illustrated example, the steps can be implemented using a suitably programmed stimulation device. It will be appreciated and understood that the steps about to be described can be implemented in the form of software instructions that are resident on a computer-readable media that is located on the stimulation device. Accordingly, aspects of the invention described herein extend to all forms of computer-readable media, whether on the stimulation device or not, when such media contains instructions that implement the methods described herein.

One assumption that the FIG. 5 flow diagram makes is that a stimulation device is configured with an automatic capture feature and that the automatic capture feature is activated.

Step 500 uses a selected electrode configuration to measure the evoked response signal. Examples of how this can be done are described above. For instance, in bipolar configurations the evoked response signal can be measured by a method that entails using the slope or slew rate of the signal to ascertain whether capture has occurred. In unipolar configurations, the evoked response signal can be measured by a method that uses the PDI to ascertain whether capture has occurred. Step 502 determines whether the selected electrode configuration is inoperative. This step can be implemented in any suitable way using any suitable techniques. One way of implementing this step is to monitor the leads that support the electrodes relative to which the evoked response signal is measured. If the impedance of the leads falls outside of a defined range, then this can indicate that the electrodes are inoperative for their intended purpose. If the electrode configuration is not inoperative, then the method branches back to step 500 and continues to use the selected electrode configuration. If, on the other hand, step 502 determines that the electrode configuration is inoperative for whatever reason, step 504 determines whether there is another electrode configuration available for measuring the evoked response signal.

As an example, consider the following. Assume that the patient has a bipolar lead that has been used for measuring the evoked response signal. Assume also that for some reason, the ring electrode of the bipolar lead malfunctions. In this case, only the unipolar configuration of that particular lead is available for measuring the evoked response signal. It should be noted that there may be other leads that have electrodes that can be used for this purpose. But for this example, assume that only the present lead's unipolar configuration can be used for measuring the evoked response signal. In this particular example, then, step 504 determines that another electrode configuration is available for measuring the evoked response signal. Accordingly, step 508 selects the other electrode configuration and step 510 configures the stimulation device for the newly selected electrode configuration to measure the evoked response signal. Configuration of the new electrode configuration can take place in any suitable manner that is typically used for that particular electrode configuration. This step can also be considered as a calibration step in which various parameters that are associated with the new electrode configuration are initialized and calibrated. If the new electrode configuration is calibrated successfully at step 512, it then branches back to step 500 and uses the newly-selected electrode configuration to measure the evoked response signal. If the new electrode configuration is not calibrated successfully, the procedure can be repeated for another electrode configuration from step 504.

If, at step 504, there is no additional electrode configuration that is available for use in measuring the evoked response signal, step 506 stops the automatic capture function. This step can involve falling back to a default setting for pacing the patient. The change can then be recorded in memory for review by a physician at the next followup.

The above-described process uses a first method to measure the evoked response signal to ascertain whether capture has occurred. If, for some reason, the first method is inoperative to function as intended, the stimulation device can automatically switch to a different method for measuring the evoked response signal. Switching to a different method can involve a recalibration process in which various parameters for a selected electrode configuration can be initialized and calibrated so that the new electrode configuration can accurately measure the evoked response signal.

Figure 6:
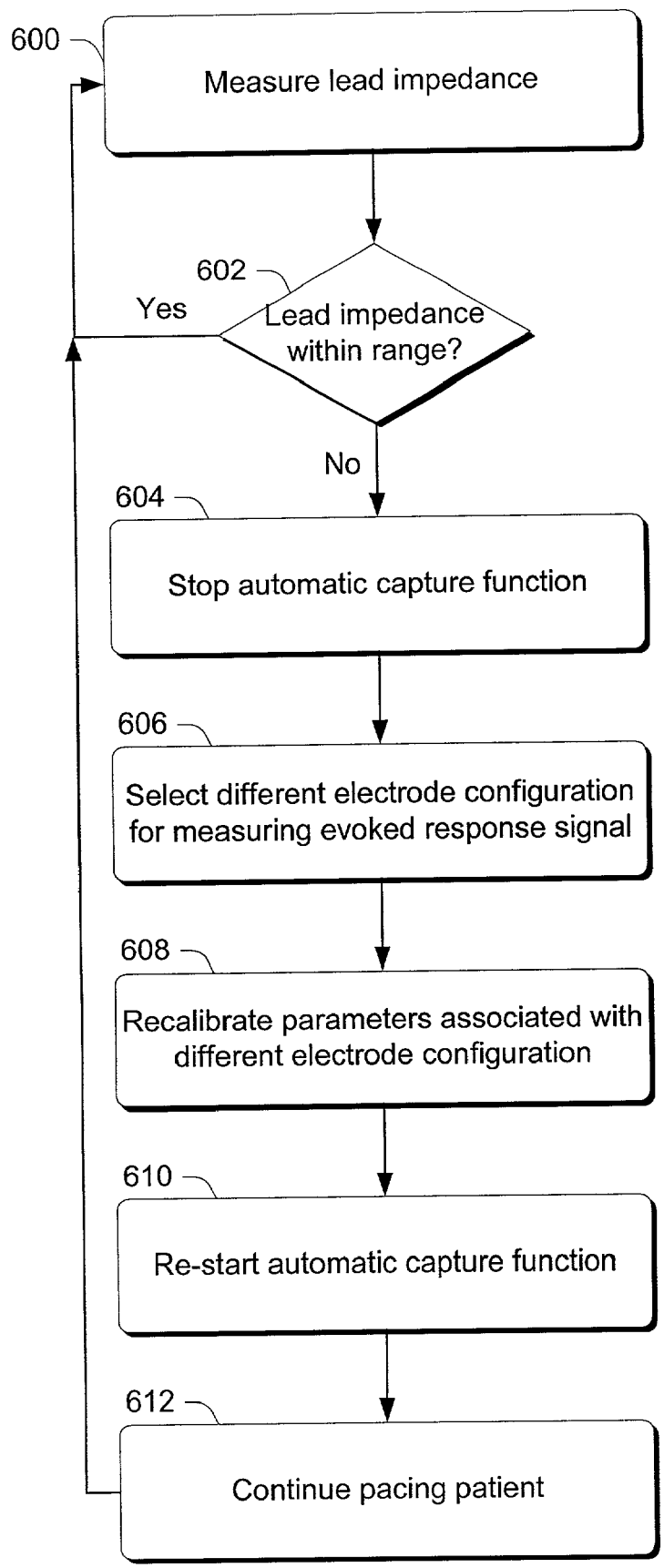
FIG. 6 is a flow diagram that describes steps in a method in accordance with one embodiment.

FIG. 6 is a flow diagram that describes steps in one embodiment of a specific evoked response measurement method. The steps can be implemented in any suitable hardware, software, firmware, or combination thereof. In the illustrated example, the steps can be implemented using a suitably programmed stimulation device.

One assumption that the FIG. 6 flow diagram makes is that a stimulation device is configured with an automatic capture feature and that the automatic capture feature is activated.

Step 600 measures lead impedance associated with one or more leads that carry electrodes that are currently being used to measure the evoked response signal. The techniques that can be used to measure lead impedance are known and are not described in additional detail here. Step 602 determines whether the measured lead impedance is within a defined range. If so, then the method branches back to step 600. If not, then step 604 stops the automatic capture feature or function. Step 606 then selects a different electrode configuration for measuring the evoked response signal (if there is one available). Step 608 recalibrates parameters associated with the different electrode configuration. The parameters that are recalibrated and the techniques for recalibrating them can vary as between different electrode configurations. Those of skill in the art will appreciate and understand the various parameters that should be recalibrated and the techniques that can be used to recalibrate them. Accordingly, such is not described in detail here. Step 610 then re-starts or re-activates the automatic capture function or feature of the stimulation device, and step 612 continues pacing the patient using the re-started automatic capture function. Step 612 then branches back to step 600 and measures the lead impedance associated with the different electrode configuration. It is to be noted that the range that is utilized to ascertain whether the impedance is acceptable can likely change with a change in electrode configuration.

Additional Examples of Electrode Configurations

In the exemplary electrode configurations discussed above and below, the evoked response signal is described in the context of being used to ascertain ventricular capture. It is to be appreciated and understood that the principles described herein can be readily adapted for use in ascertaining atrial capture as well.

Figure 7:
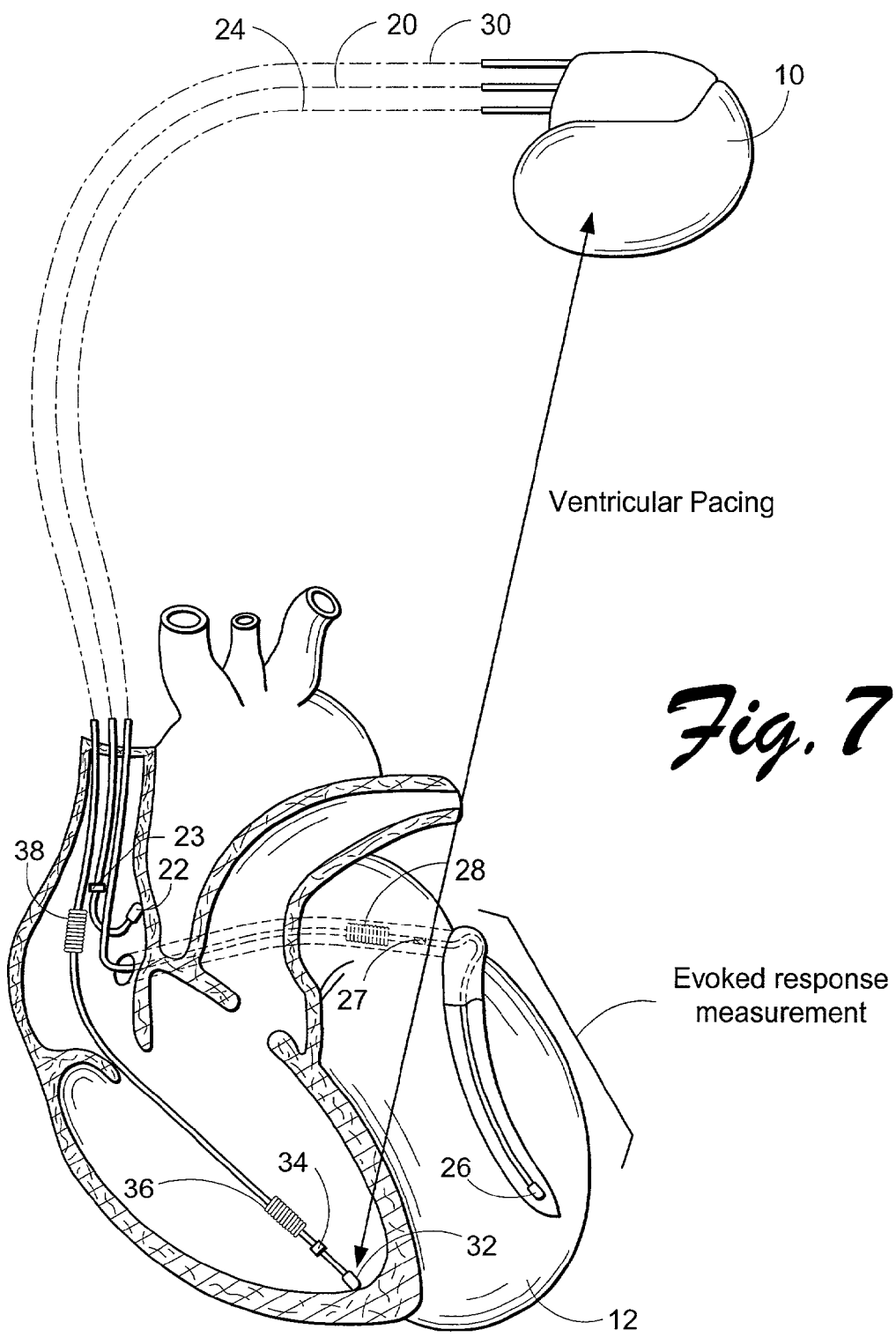
FIG. 7 is a diagram of the FIG. 1 stimulation device and illustrates another exemplary electrode configuration for ascertaining whether ventricular capture has occurred.

FIG. 7 shows the FIG. 1 stimulation device configured in a manner such that ventricular pacing takes place using a unipolar configuration in the right ventricle (i.e. between tip electrode 32 and the case), while the evoked response signal is measured using a bipolar configuration with the lead in the left ventricle (i.e. between the ring electrode 27 and the tip electrode 26). In this particular configuration, the slope or slew rate of the evoked response signal can be used to ascertain whether capture has occurred.

Figure 8:
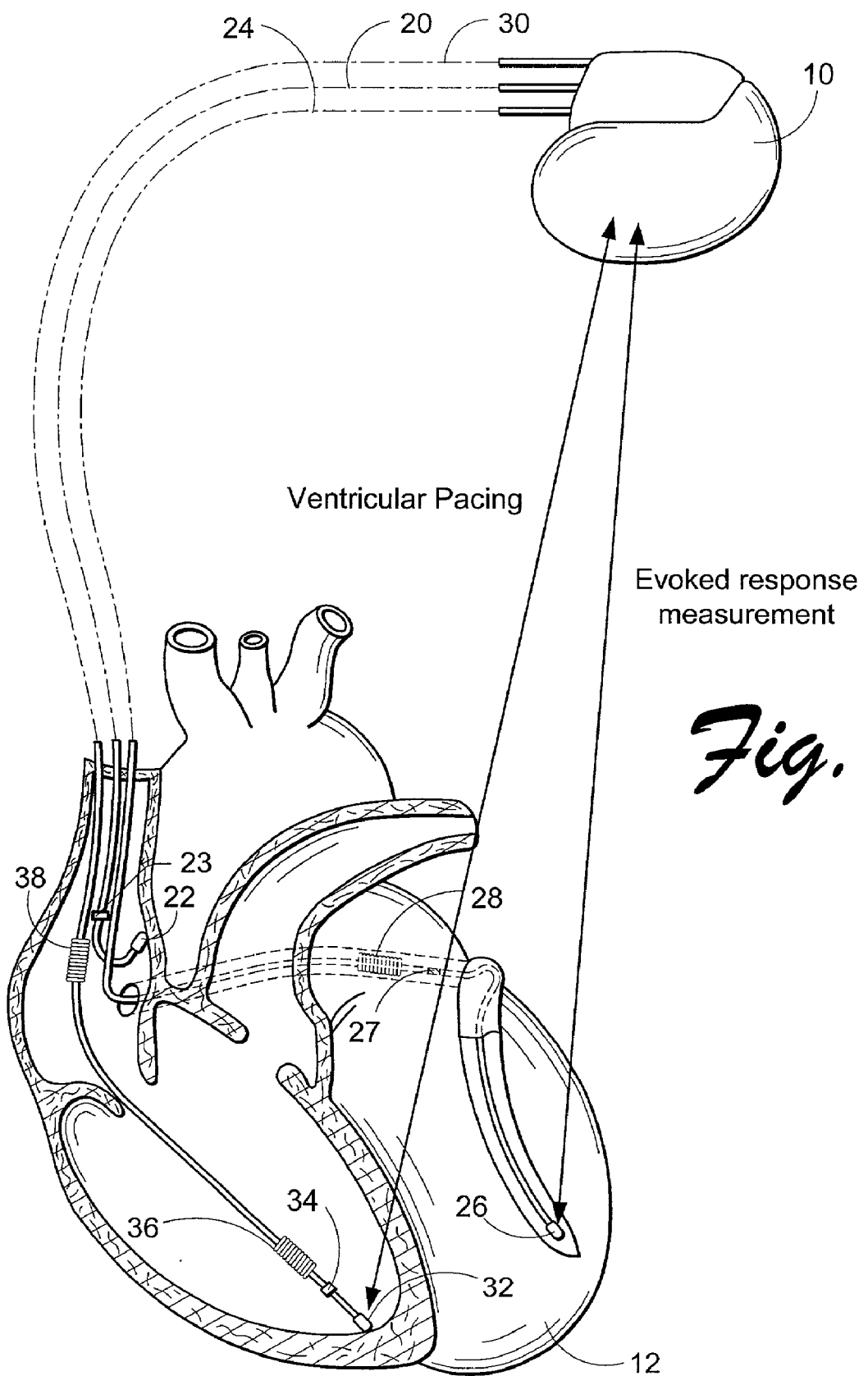
FIG. 8 is a diagram of the FIG. 1 stimulation device and illustrates another exemplary electrode configuration for ascertaining whether ventricular capture has occurred.

FIG. 8 shows the FIG. 1 stimulation device configured in a manner such that ventricular pacing takes place using a unipolar configuration in the right ventricle (i.e. between tip electrode 32 and the case), while the evoked response signal is measured using a unipolar configuration with the lead in the left ventricle (i.e. between the tip electrode 26 and the case).

It is to be appreciated and understood that the above-described electrode configurations for measuring the evoked response signal constitute but examples only. It is possible for other combinations of electrodes to be used in, for example, other types of devices. It is intention of the above description to provide but a few illustrative examples that illustrate the inventive concepts.

Selecting a Preferred Electrode Configuration for Measuring Evoked Response

There are instances when, due to the number of electrodes associated with a particular stimulation device, multiple different permutations of electrode configurations are possible for purposes of measuring or detecting the evoked response signal to ascertain whether capture has occurred (both ventricular capture and atrial capture). In these instances, there may be certain configurations that are better than others. For example, perhaps there are three suitable electrode configurations that can be used to measure the evoked response signal, but, for whatever reason, one of them can provide better data. In this case, it is highly desirable to select the one configuration that provides the best data.

Figure 9:
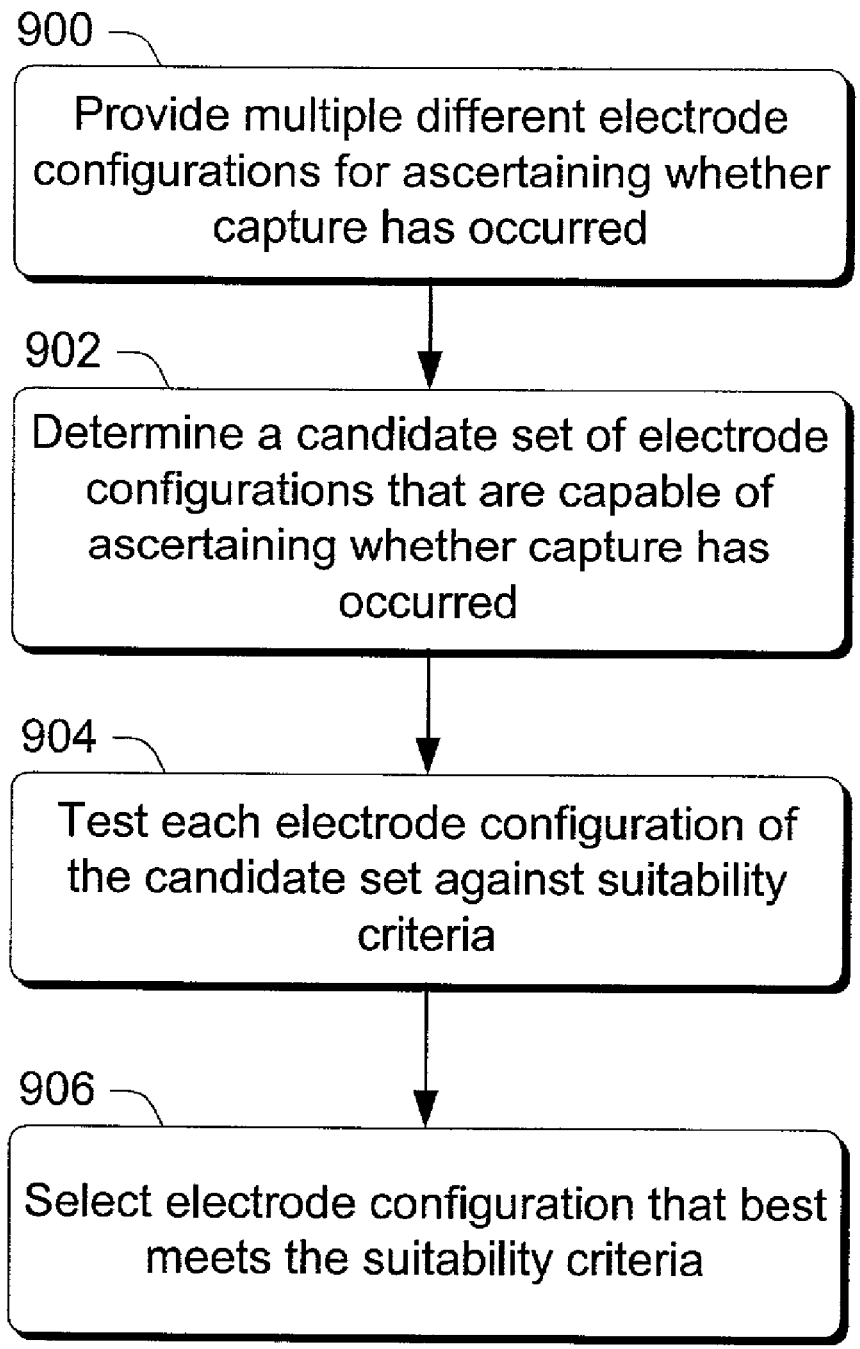
FIG. 9 is a flow diagram that describes steps in a method in accordance with one embodiment.

FIG. 9 is a flow diagram that describes steps in a method in accordance with one embodiment. The steps can be implemented in any suitable hardware, software, firmware, or combination thereof. In the illustrated example, the steps can be implemented automatically, using a suitably programmed stimulation device.

Step 900 provides multiple different electrode configurations for ascertaining whether capture has occurred. The capture can be either an atrial capture or ventricular capture. Some exemplary electrode configurations for ascertaining whether ventricular capture has occurred are given above. Step 902 determines a candidate set of electrode configurations that are capable of ascertaining whether capture has occurred. This step can be implemented by monitoring the various electrodes, as by a lead supervision feature that measures the impedance of the leads, to ascertain whether the electrodes are in a condition to be used for ascertaining capture. This step can be implemented in a periodic manner where the various electrode configurations are tested for their integrity. Alternately, this step can be implemented when there is a need to transition to a different electrode configuration for ascertaining capture. Step 904 tests one or more, and preferably each electrode configuration of the candidate set against suitability criteria. Exemplary suitability criteria can be established based on considerations that include how well the configuration is able to develop data, the integrity of the developed data, various complexities involved in developing the data and the like. Step 906 then selects an electrode configuration that best meets the suitability criteria.

In practice, portions of this method can be implemented while the automatic capture feature of the stimulation device is turned off. For example, assume that step 902 is implemented in response to a current electrode configuration failure. Typically, upon failure of the current electrode configuration, the automatic capture feature can be turned off. Steps 904 and 906 can then be performed while the automatic capture feature is turned off. At the conclusion of step 906 (and, of course the performance of any calibration procedures), the automatic capture feature can be turned back on with the selected electrode configuration being used to ascertain whether capture has occurred.

In other embodiments, electrode configurations can be automatically switched in connection with functionalities other than for ascertaining capture. For example, automatic switching and calibration of electrode configurations can be used in connection with ascertaining a patient's minute ventilation. In this context, then, the methodology can include providing a desired functionality using the implantable device and then automatically stopping the desired functionality. The electrode configuration can be switched to a new electrode configuration and calibrated for the new configuration. Once calibrated, the electrode configuration can be used to provide the previously stopped functionality. That is, the previously stopped functionality can be re-started using the new electrode configuration. Such other functionalities can include, without limitation, autosensitivity, PVARP and PVAB, to name just a few.

CONCLUSION

The various embodiments described above permit electrode configurations that are used to ascertain capture to be automatically changed, and for parameters associated with those configurations to be automatically calibrated so that a stimulation device's automatic capture feature can continue to function notwithstanding the fact that an electrode configuration change has taken place. This promotes convenience and flexibility on the part of heart patients in whom the stimulation devices are implanted.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. A method for measuring an evoked response signal to allow automatic capture detection to automatically continue functioning upon an automatic change of a sensing electrode configuration of an implantable stimulation device, the method comprising:

automatically determining whether a current sensing electrode configuration that is being used to measure an evoked response signal to ascertain whether capture has occurred is unable to be used for that purpose;

automatically switching to at least one other different sensing electrode configuration to measure the evoked response signal to ascertain whether capture has occurred;

performing an automatic recalibration procedure with the different sensing electrode configuration; and automatically using the different sensing electrode configuration to measure evoked response signals to allow the automatic capture detection to continue functioning upon the automatic change of a sensing electrode configuration.

2. The method of claim 1, wherein at least one of the electrode configurations comprises a bipolar configuration.

3. The method of claim 1, wherein at least one of the electrode configurations comprises a unipolar configuration.

4. The method of claim 1, wherein said using comprises using the different electrode configuration to ascertain whether ventricular capture has occurred.

5. The method of claim 1, wherein said using comprises using the different electrode configuration to ascertain whether atrial capture has occurred.

6. A stimulation device configured to implement the method of claim 1.

7. The method of claim 1, wherein said performing a recalibration procedure comprises processing evoked response signals by examining a slope or slew rate of the evoked response signal for a unipolar sensing electrode configuration, and wherein said performing a recalibration procedure comprises processing evoked response signals by examining a paced depolarization integral of the evoked response signals for a bipolar sensing electrode configuration.

8. One or more computer-readable media having computer-readable instructions thereon which, when executed by a programmable stimulation device, cause the stimulation device to:

determine whether a current sensing electrode configuration that is being used to measure an evoked response signal to ascertain whether capture has occurred is unable to be used for that purpose;

automatically switch to at least one other different sensing electrode configuration to measure the evoked response signal to ascertain whether capture has occurred;

automatically perform a recalibration procedure with the different sensing electrode configuration; and automatically use the different sensing electrode configuration to measure the evoked response signal to allow automatic capture detection to automatically continue functioning upon an automatic change of a sensing electrode configuration.

9. The one or more computer-readable media of claim 8, wherein at least one of the electrode configurations comprises a bipolar configuration.

10. The one or more computer-readable media of claim 8, wherein at least one of the electrode configurations comprises a unipolar configuration.

11. The one or more computer-readable media of claim 8, wherein the instructions cause the stimulation device to use the different electrode configuration to ascertain whether ventricular capture has occurred.

12. The one or more computer-readable media of claim 8, wherein the instructions cause the stimulation device to use the different electrode configuration to ascertain whether atrial capture has occurred.

13. The one or more computer-readable media of claim 8, wherein said causes the stimulation device to automatically perform a calibration procedure comprises processing evoked response signals by examining a slope or slew rate of the evoked response signals for a unipolar sensing electrode configuration, and wherein said causes the stimulation device to automatically perform a recalibration procedure comprises processing evoked response signals by examining a paced depolarization integral of the evoked response signals for a bipolar sensing electrode configuration.

14. A stimulation device comprising:
one or more computer-readable media;
one or more processors; and
instructions resident on the computer-readable media, which, when executed by the one or more processors, cause the one or more processors to:
determine whether a current sensing electrode configuration that is being used to measure an evoked response signal to ascertain whether capture has occurred is unable to be used for that purpose;
automatically switch to at least one other different sensing electrode configuration to measure the evoked response signal to ascertain whether capture has occurred;
automatically perform a recalibration procedure with the different sensing electrode configuration; and
use the different sensing electrode configuration to measure the evoked response signal to allow automatic capture detection to continue functioning upon an automatic change of a sensing electrode configuration.

15. The stimulation device of claim 14, wherein at least one of the electrode configurations comprises a bipolar configuration.

16. The stimulation device of claim 14, wherein at least one of the electrode configurations comprises a unipolar configuration.

17. The stimulation device of claim 14, wherein said instructions cause the one or more processors to use the different electrode configuration to ascertain whether ventricular capture has occurred.

18. The stimulation device of claim 14 wherein said instructions cause the one or more processors to use the different electrode configuration to ascertain whether atrial capture has occurred.

19. The stimulation device of claim 14, wherein said instructions cause the one or more processors to automatically perform a recalibration procedure comprises processing evoked response signals by examining a slope or slew rate of the evoked response signal for a unipolar sensing electrode configuration, and wherein said instructions cause the one or more processors to automatically perform a recalibration procedure comprises processing evoked response signals by examining a paced depolarization integral of the evoked response signals for a bipolar sensing electrode configuration.

20. A method of operating an implantable stimulation device to allow automatic capture detection to continue functioning upon an automatic change of a sensing electrode configuration, the method comprising:
providing, with an implantable stimulation device, a desired functionality that utilizes, at least in part, a first sensing electrode configuration;
automatically stopping, with the implantable stimulation device, the desired functionality;
automatically switching, with the implantable stimulation device, to a second sensing electrode configuration;
automatically calibrating the second sensing electrode configuration; and
automatically restarting, with the implantable stimulation device, the desired functionality utilizing, at least in part, the second sensing electrode configuration to allow automatic capture detection to continue functioning upon a change of a sensing electrode configuration.

21. The method of claim 20, wherein said automatically calibrating the second sensing electrode configuration comprises processing evoked response signals by examining a slope or slew rate of the evoked response signal for a unipolar sensing electrode configuration, and wherein said automatically calibrating the second sensing electrode configuration comprises processing evoked response signals by examining a paced depolarization integral of the evoked response signals for a bipolar sensing electrode configuration.

22. A stimulation device comprising:
means for providing an automatic capture feature;
means for providing a first sensing electrode configuration that can be used to measure an evoked response signal to provide a measurement that is used by the automatic capture feature means; and
means for automatically switching the first sensing electrode configuration to a different sensing electrode configuration;
means for automatically recalibrating one or more parameters associated with the different sensing electrode configuration; and
means for using the different sensing electrode configuration to measure the evoked response signal to allow the automatic capture feature means to continue functioning upon an automatic change of a sensing electrode configuration.

* * * * *